United States Patent
Chatenever et al.

(10) Patent No.: US 6,397,286 B1
(45) Date of Patent: May 28, 2002

(54) ARRANGEMENT FOR THE CENTRAL MONITORING AND/OR CONTROL OF AT LEAST ONE APPARATUS

(75) Inventors: David Chatenever, Santa Barbara, CA (US); Klaus Irion, Emmingen-Liptingen (DE); Pavel Novak, Schaffhausen (CH); Hans-Uwe Hilzinger, Tuttlingen (DE)

(73) Assignee: Storz Endoskop GmbH (CH)

( * ) Notice: Subject to any disclaimer, the term of this patent is extended or adjusted under 35 U.S.C. 154(b) by 0 days.

(21) Appl. No.: 09/180,692

(22) PCT Filed: Mar. 12, 1998

(86) PCT No.: PCT/EP98/01445

§ 371 (c)(1),
(2), (4) Date: May 3, 1999

(87) PCT Pub. No.: WO98/40822

PCT Pub. Date: Sep. 17, 1998

(30) Foreign Application Priority Data

Mar. 12, 1997 (DE) .......................................... 197 10 191
Jul. 22, 1997 (DE) .......................................... 197 33 005

(51) Int. Cl.[7] .............................................. G06F 13/00
(52) U.S. Cl. ...................................... 710/302; 600/118
(58) Field of Search ................................ 710/100, 101, 710/126, 129, 103, 300, 302, 305; 600/110, 118, 132, 109, 103, 117, 101; 606/1, 4, 6, 10, 11, 12, 14, 15, 16

(56) References Cited

U.S. PATENT DOCUMENTS

| | | |
|---|---|---|
| 4,688,168 A | 8/1987 | Gudaitis et al. |
| 4,774,568 A | 9/1988 | Matsuo |
| 4,870,704 A | 9/1989 | Matelan et al. |
| 5,777,602 A * | 7/1998 | Schaller et al. .............. 345/157 |
| 5,877,819 A * | 3/1999 | Branson ...................... 348/701 |
| 6,224,542 B1 * | 5/2001 | Chang et al. ............... 600/109 |

FOREIGN PATENT DOCUMENTS

| | | |
|---|---|---|
| DE | 37 41 833 C1 | 4/1989 |
| DE | 92 18 373.5 | 3/1994 |
| EP | 0 319 762 A1 | 6/1989 |
| EP | 0 355 042 A2 | 2/1990 |
| EP | 0 567 354 A1 | 10/1993 |
| EP | 0 568 081 A1 | 11/1993 |
| JP | 62-46182 | 2/1987 |
| WO | WO 94/23375 | 10/1994 |
| WO | WO 95/22363 | 8/1995 |

* cited by examiner

Primary Examiner—Glenn A. Auve
(74) Attorney, Agent, or Firm—St. Onge Steward Johnston & Reens LLC

(57) ABSTRACT

What is described here is a system for centrally monitoring and/or controlling at least one unit for endoscopy and particularly for minimally invasive surgery, such as an insufflation means, a pump, a light source and/or a video camera, wherein the unit or units to be controlled are interconnected via interfaces.

The inventive system is characterised by the combination of the following features:
 the units are connected via the interfaces on a self-configuring bus to a BUS master,
 the BUS master configures the bus automatically,
 the BUS master monitors the communication on the bus for correct execution.

40 Claims, 2 Drawing Sheets

ARRANGEMENT FOR THE CENTRAL MONITORING AND/OR CONTROL OF AT LEAST ONE APPARATUS

FIELD OF THE INVENTION

The present invention relates to a system for centrally monitoring and/or controlling at least one unit for endoscopy, and specifically for minimal invasive surgery, in accordance with the introductory clause of Patent claim 1.

PRIOR ART

Systems for centrally monitoring and/or controlling endoscopic units are known, for instance, from the European Patent EP 0 319 762 A1 or the German Patent DE 37 41 833 C1 of the same priority, the U.S. Pat. No. 5,627,584, the international patent WO 95/22363, the Japanese Patent A 62-46182 or the German Utility Model U1 92 18 373. Explicit reference is made to these prior art documents as far as all other details are concerned which are not explained here in all their details.

The known systems of the type which the introductory clause of Patent claim 1 starts out from may be employed, for instance, for controlling one or several insufflation units, pumps, an illuminating device for the image field of an endoscope, an HF instrument for cutting or coagulation, or a laser.

In the systems known from the aforementioned prior art documents the unit to be controlled is connected to a master computer via an interface (serial or parallel interface in EP 0 319 762 A1) or a network (e.g. DE 92 18 373 U1) which controls the device and displays the operating parameters of the unit on a monitor.

Moreover, a similar system is known from the European Patent EP 0 568 081 A1, which is, however, intended for an examination and/or treatment of the eyes.

The use of serial or parallel interfaces for controlling the devices presents the disadvantage that the number of the total of units which can be controlled by the master computer is restricted by the number of computer interfaces. This number is comparatively small particularly on a standard PC.

Networking, on the other hand, requires the application of "comparatively intelligent" units so that the expenditure is increased for the central control on the device side. Moreover, in standard networks, which are implemented, for instance, on the basis of network operating systems such as Novell, it is comparatively difficult to log in or off a unit during operation. This may be necessary in medical operations, for instance, when a unit fails and must be replaced by a unit of the same type, or when a certain surgical condition demands the connection of another unit. Apart therefrom, the known network solutions are not failsafe to such a high degree that they could be employed in the operating theatre.

But even if only a comparatively small number of units is centrally controlled the following problem always occurs whenever more than one unit is controlled:

The operator wants to change the operating parameters—e.g. of unit 1—but fails to be aware of the fact that this unit operates in the control mode for unit 2—for instance. In such a situation the operator resets the operating parameters for this unit unintentionally. But even if this error is noticed immediately it is frequently difficult to "reset" the operating parameters again to "reasonable" values.

BRIEF DESCRIPTION OF THE INVENTION

The present invention is based on the problem of improving a system for centrally monitoring and/or controlling at least one unit for endoscopy, and specifically for minimally invasive surgery, in accordance with the introductory clause of Patent claim 1 in such a way that a large number of (different or identical) units can be centrally controlled at a comparatively low expenditure, specifically in terms of the units to be controlled, with the replacement of failed units or the connection of new units being possible during the ongoing operation without any problems and particularly without interference with the other units.

Moreover, the inventive system should preferably be so designed that erroneous operation may be simply corrected and particularly annulled, even if already various other interventions have been performed on the controller of the units.

One inventive solution to this problem is obtained with the combination of features defined in claim 1. Improvements of the invention are the subject matters of claims 2 et seq.

The invention is distinguished by the combination of the following features:

the units are connected via the interfaces on a self-configuring bus to a BUS master, the BUS master configures the bus automatically, and the BUS master monitors the communication on the bus for correct functioning.

It is hence possible to connect or disconnect units during operation so that the "network" can adapt itself to varying situations in a surgical operation, for instance. It is also possible in particular to replace failed units.

It is a particular advantage that the BUS reconfigures itself during operation when units are newly connected or disconnected. This is accompanied by the additional advantage that the bus is automatically terminated.

The most different solutions may be employed as bus; one possibility is the application of the so-called FireWire bus in compliance with IEEE standard 1394. Another preferred possibility is the use of the CAN bus:

The CAN bus (Controller Area Network), which has been developed by the company of Robert Bosch, Germany, and is standardised in compliance with ISO and IEEE, presents not only the advantages of a high immunity to noise and simple wiring with a 2-conductor technique, but mainly the advantage that on account of the low software expenditure it is possible to connect also units with plain 8-bit controllers. Moreover, the CAN bus is suitable for real-time operation and permits a multi-master structure. Both the versions under ISO 11898 and the versions in compliance with ISO 11519/11898 can be applied.

On account of these features the expenditure incurred for the modification of conventional units for application with a central control system is comparatively low.

With such a design both BUS arbitration and data communication can be implemented, in particular, via a two-wire line so that the expenditure in terms of wiring is particularly low.

In certain cases—e.g. with application of a remote control system—is it preferable to implement the bus link at least between one part of the units by means of an infrared or radio transmission link instead of a "fixedly wired" link.

The bus interface can be supplied with power either via the respective unit or via the bus line, without any interruption of communication on the bus, when a unit connected to the bus is switched off or is not switched on. In particular, the power supply of the interface may be provided via the bus line by means of lines which are not required for communication. Moreover, one or several units may supply the interfaces of the remaining units with power.

The operating safety is further enhanced, specifically when HF units etc. are employed, when the interface is galvanically isolated from the respective unit.

When a remote control system is applied it is expedient that the remote controller is suitable for controlling more than one unit. The remote controller should be designed in a way that it can be used under sterile conditions. Consequently, the operating physician can control the units himself without any problem and without depending on an aide. In an approach to avoid operating errors it is preferable that the changes made by an operator, and particularly the changes made via the remote controller, are graphically or possibly acoustically indicated or displayed, respectively.

As has been set out above already, it is an advantage to provide a bus suitable for multi-master operation. With such a configuration at least one of the following units may be configured as BUS master:

video signal processing unit master computer remote control unit network module.

The network module may be adapted for connection and particularly docking to each unit adapted for connection to the bus so that it is not necessary to use a PC or any other controller having master capabilities in the network. The network module may be connected in particular via a serial interface.

Whenever more than one unit suitable for use as BUS master is connected to the bus provisions should preferably be made for arbitration or assignment of priorities so as to ensure that only one BUS master assumes the active BUS master function.

In another preferred improvement of the invention the BUS master is a master computer, particularly an IBM-compatible or so-called industrial standard PC, with a bus interface. The master computer may operate specifically in a programming and an application mode. In programming mode the operating parameters of the units to be controlled can be preset and the preset values can be stored whereas in application mode the operating parameters can be changed only currently without influence on the fundamental setting.

With these provisions the problem is solved that in case of application of a central controller unintentionally the "wrong unit" is operated and thus reset.

It is preferable that in programming mode the performance of a medical operating procedure is not possible.

In case of an operating error the operator has thus always the possibility to "return" to the invariable fundamental setting during the operation, in which the system is operating in the application mode. This procedure is substantially safer than the design in which for reset of a value the respectively last value must be called in as this value may have already been changed unintentionally by an operating error and in a way unsuitable for the respective medical treatment.

In view of the different cases which may occur, for instance, in medical operations, it is moreover preferable that several different preset values may be stored for each unit to be controlled, which the operator can then call in in correspondence with the actual situation.

The software may be so designed that each unit connected to the bus can be individually configured. This provision permits, for instance, the individualised configuration or calibration of different units of the same type.

It is furthermore expedient for monitoring and logging—particularly in the event of damage—to design the software in such a way that the user of the system can be unambiguously identified. This may be achieved, for example, by the provision that the user must enter his identification when he starts the inventive system, and that this identification is then stored and logged.

As various users have frequently different "preferences" for the setting of the individual units the entered identification of the respective user may change the fundamental system setting in another expedient embodiment.

Moreover, the software may be so designed that the preset state of the units connected to the bus, which is required for a specific operation, can be stored.

Operation is even further facilitated when the master computer has a graphic user interface which is suitable for intuitive operation in particular. Such user interfaces are, for instance, Windows 3.1, 95, NT or their successors, or the corresponding interfaces of OS/2 or Unix systems, respectively, such as Windows X. Other operating systems such as OS9 etc. may, of course, also be used.

The operation of the units in stress situations which occur again and again specifically in surgical operations is further facilitated when the user interface displayed on a monitor of the master computer may be configured by the operator It is hence possible to display only those operating elements which are required for the respective operating procedure whilst the remaining operating elements are masked so that the risk of operating errors is further reduced.

For support of users who have so far no experience with computer-supported equipment in acquainting themselves with such systems it is furthermore preferred that the operating elements of at least one conventional unit, such as ON/OFF switches, slides or control buttons or any other function keys are graphically reproduced on the monitor displaying the user interface. It is particularly preferable that the displayed operating elements resemble the operating elements on conventional equipment in terms of their appearance so that the user need not acquaint himself with an uncommon element.

It is furthermore possible to display the operating elements of several units simultaneously on the monitor so that even complex treatments can be performed in a simple manner.

In order to avoid the unintentional resetting of parameters it is moreover expedient to display merely a selection of operating elements of the unit or units at the same time, which the operator can configure himself. With these provisions it is specifically possible to vary merely certain parameters of the units connected to the bus, in correspondence with the respectively called-in presetting.

The master computer can be controlled, for instance, by means of a mouse, a joy stick, a roller ball, a touch screen or similar element. In any case it is expedient that the elements provided for operation are so configured that they are suitable for application under sterile conditions. This may be achieved, for instance, by the fact that the elements as such can be sterilised or that they are provided with a sterile coating.

It is furthermore possible to control the functions which can be controlled via the bus via a speech-input and processing module. In such a case it is preferred that the speech commands are graphically displayed on a monitor or are acoustically confirmed so that the operator can recognise and correct possibly misunderstood commands. This is facilitated by the provision that incorrectly input commands or control sequences can be cancelled immediately.

In another preferred improvement of the invention a video signal processing unit is provided to which the video signal from a digital or analog video camera is applied and which may include specifically a video processor. The video signal processing unit can then display the image produced by the video camera in a window on the graphic user interface of the master computer.

It is furthermore possible that the video signal processing unit converts the image taken by the video camera into digital data and stores them in a control computer where the general data on the patient as well as unit parameters can be stored with allocation to the stored images. This allows not only for safe and reliable filing of the data so produced but also for their patient-specific assignment and for reproduction in the case of possible damage.

The master computer is suitable to control the signal processing in the video unit via the bus, e.g. the CAN bus. To this end the video unit may include a microprocessor which controls the video signal processing and possibly a graphics processor which overlays data and/or an overlay image into the actually taken video image.

In particular. the video camera and the video monitor may be connected to the video unit directly rather than via the CAN bus.

The video signal processing unit is suitable for displaying the image taken by the video camera on an analog monitor and possibly also the information received via the bus in a video overlay on the analog monitor. The representation on the monitor of the master computer is moreover possible in a video overlay or in a window in which a digitised image is displayed. The video overlay may be configured by the user.

Furthermore, the change of settings performed via the remote control system may be graphically displayed on the monitor of the master computer or by means of a video overlay.

In a preferred improvement of the invention at lest two units are interconnected via the bus to form a closed-loop control circuit which is suitable to superpose specifically unit-internal controls. For avoidance of "interference" it is preferred that the control circuit established via the bus has a substantially smaller time constant that the unit-internal control system.

The units interconnected via the bus to form a closed-loop control circuit may be an insufflation and a suction means a source of light and a video camera, and/or a pressure gauge unit and a pump or an insufflator in particular.

It is preferred in any case that the software be so designed that software or even hardware failure will be reliably displayed for the user so that a standard operating system and a standard hardware may be used without any loss in terms of reliability and safety.

BRIEF DESCRIPTION OF THE DRAWING

The following is an exemplary description of the invention in more details with reference to the drawing wherein.

DESCRIPTION OF EMBODIMENTS

FIG. 1 shows various possible configurations of the network used in accordance with the present invention.

Figure 1A:
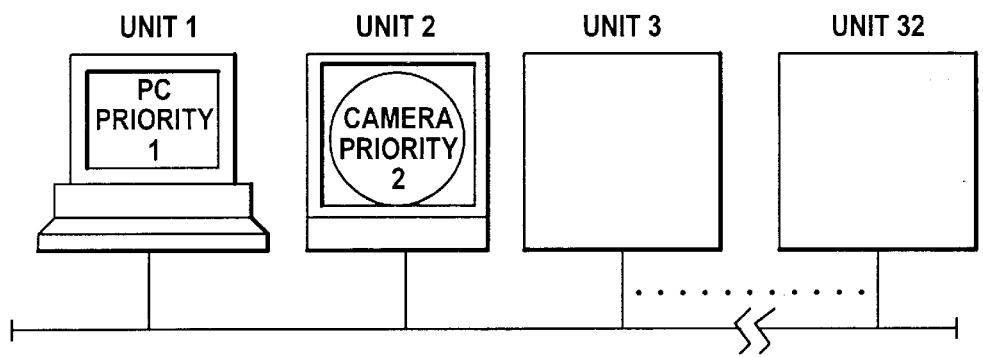
FIGS. 1a–1d illustrate different network configurations.

FIG. 1a shows as first possibility the case where a master computer PC (unit 1) serves as network master whereas a camera controller or a video signal processor (unit 2), respectively, is used as monitor. The units 3 to 32, e.g. insufflators, pumps, HF surgical equipment, light sources, etc., are connected as network slaves.

Figure 1B:
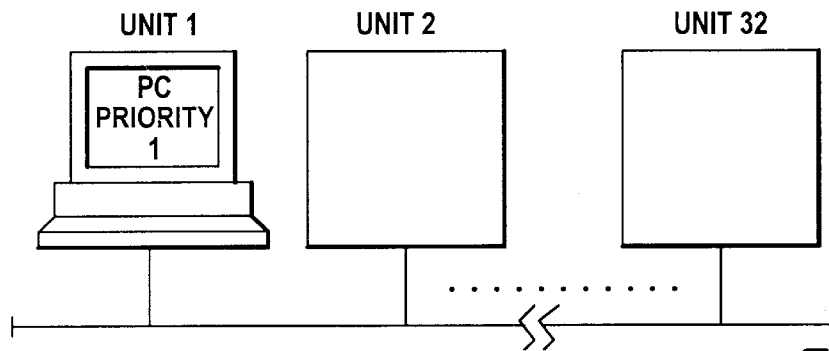

FIG. 1b illustrates as second possibility the case where a master computer PC (unit 1) is used as network master and monitor whereas all other units 2 to 32 are connected as network slaves.

Figure 1C:
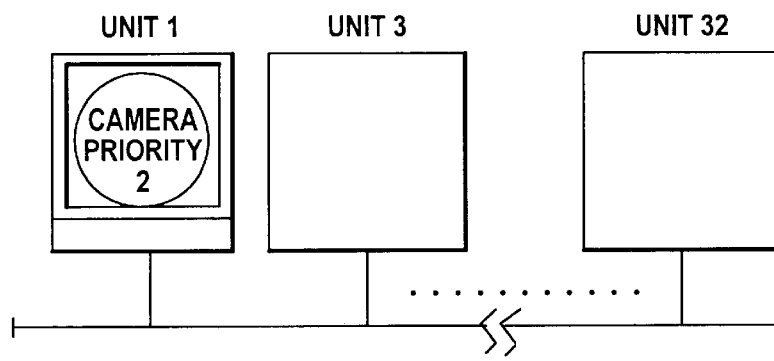
Figure 1D:
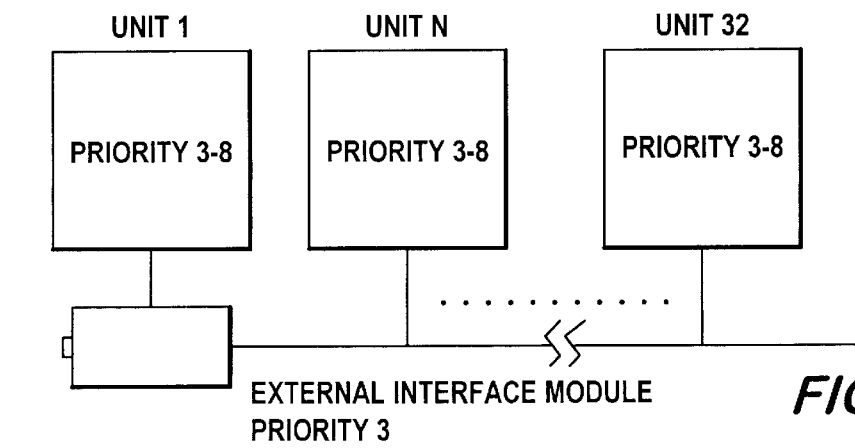

FIG. 1c eventually shows as third possibility the case where the camera controller (unit 1) is used as both network master and monitor whereas all other units 2 to 32 are again connected as network slaves, FIG. 1d is a view of the case that an external interface module is connected as network master, without the provision of a monitor. The units 1 to 32 are connected as network slaves.

In the event that the master computer (PC), the camera controller (camera) and the external interface module are provided in a network at the same time these elements are assigned different priorities so that only one unit serves as bus master at a time. In the illustrated embodiment the master computer has a higher priority than the camera controller and the interface module whilst the camera controller has precedence as bus maser over the interface module.

Figure 2:
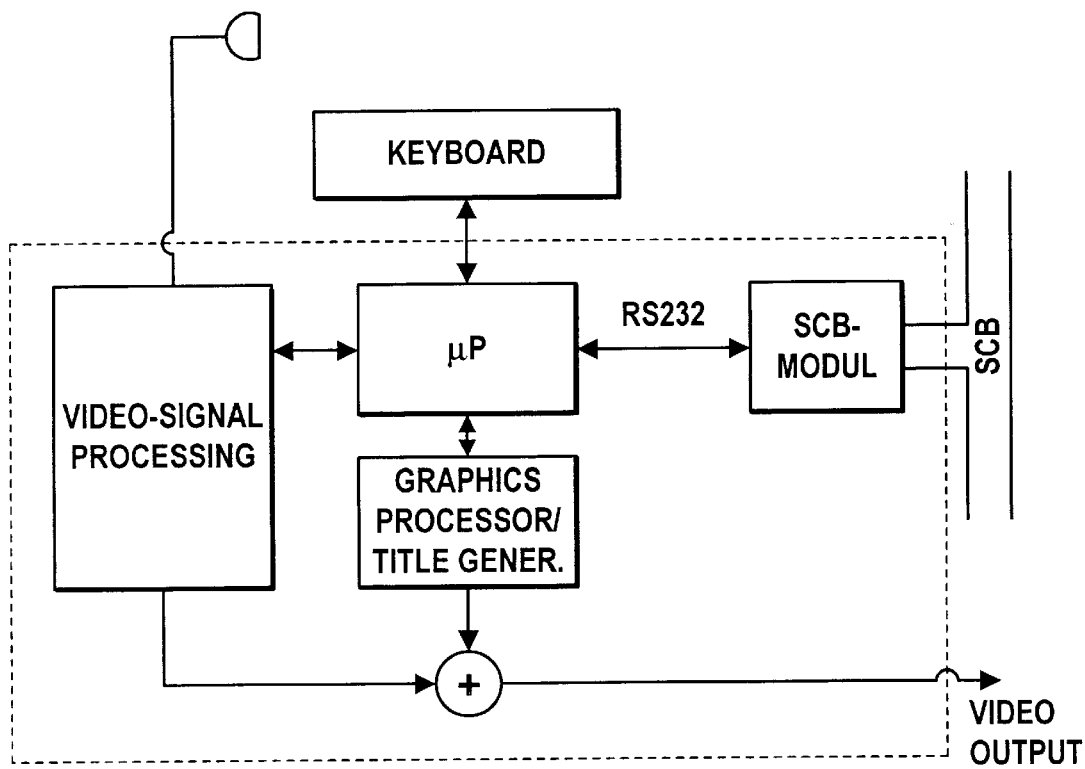
FIG. 2 shows an inventive system with video signal processing system.

FIG. 2 shows an embodiment of an inventive system with video signal processing provisions. A microprocessor or a micro-controller $\mu P$ is provided as central controller. Via an RS 232 interface—possibly also a FIFO or a dual ported RAM—the microprocessor $\mu p$ is connected to an interface module (SCB module) which is configured in correspondence with the selected bus, e.g. a CAN bus, and is provided with elements for bus control and communication and possibly with elements for galvanic isolation, such as optocouplers. In the illustrated embodiment a keyboard (keyboard) is provided for control of the microprocessor $\mu P$.

The microprocessor $\mu P$ controls, on the one hand, a video signal processor (Videosignal Processing) to which the camera signal is applied, and receives, on the other hand, data from the video signal processor for storage and/or filing via the bus in a patient data file on a computer, for instance.

Moreover, the video signal processor controls a graphics processor (Graphics Processor, Title Generator) which is suitable to generate information including a video overlay, which the user can configure, on a monitor which is not illustrated.

The output signals from the video signal processor and the graphics processor as heterodyned as video output signal and output independently by the bus and stored, for instance, on an analog or digital monitor and/or stored on a computer.

Figure 3:
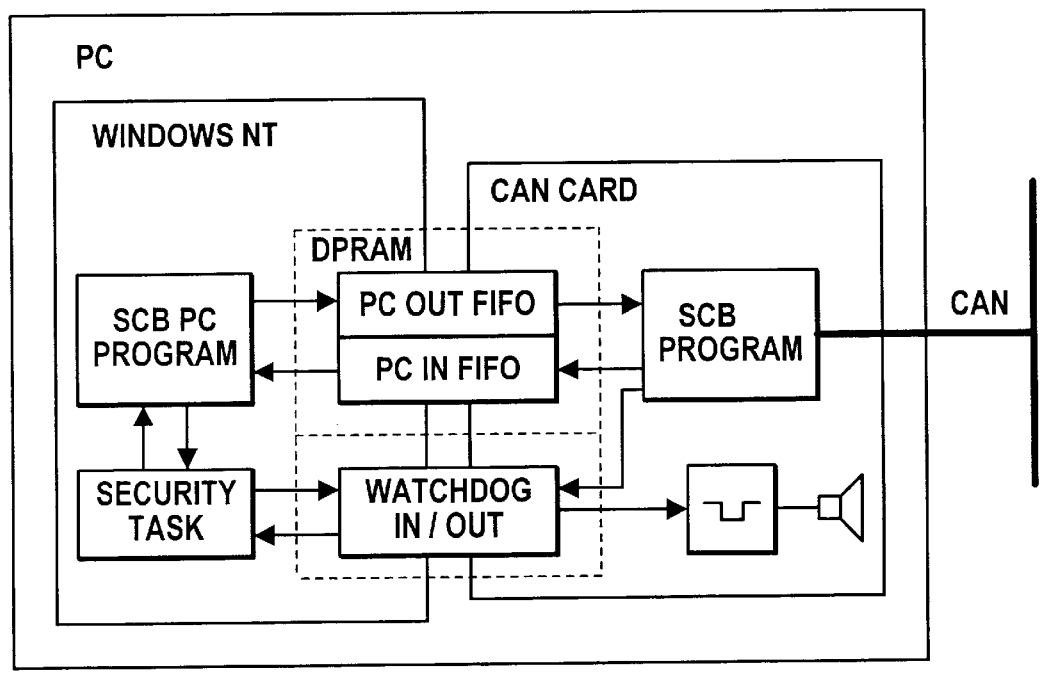
FIG. 3 represents an implemented form of the inventive safety concept.

FIG. 3 illustrates an implemented embodiment of the inventive safety concept. A master computer (PC), which executes, for instance, the bus master control programme under Windows NT, is connected to an interface board (CAN card) via a FIFO or a dual ported RAM. A so-called security task is additionally provided for cyclic exchange of information between the master computer and the interface board. When the security task establishes that the data communication is erroneous an alarm is produced. To this end an acoustic alarm generator is provided in the interface board. In all other structural respects reference is made to FIG. 3.

The invention has been described in the foregoing by the example of embodiments without any restriction of the general inventive idea. The most different modifications are, of course, possible within the scope of this inventive idea which can be derived from the claims:

For example, the most different bus systems may be used on the condition that they are self-configuring and that the BUS master is able to configure the bus automatically and monitor the communication on the bus for correct execution.

What is claimed is:

1. System for centrally controlling a plurality of instruments for endoscopy characterized by:
    a self-configuring bus and a bus master and a plurality of interfaces interconnecting the instruments to the self-configuring bus;
    the instruments being operatively connected via interfaces on the self-configuring bus to said bus master,
    the bus master monitoring communication on the bus for correct execution;
    the bus master configuring the bus automatically whenever a said instrument is either newly connected or is disconnected from said bus without interruption of the operation of the system.

2. System according to claim 1, characterized in that said self-configuring bus is a CAN bus.

3. System according to claim 1, characterized in that a two-wire communication line effectively interconnects said bus master to said instruments wherein bus arbitration and data communication take place via said two-wire line.

4. System according to claim 1, characterized with a wireless communication link coupled to fink the bus to at least one of the instruments.

5. System according to claim 1, characterized in that the supply of power to the bus is implemented via bus lines not required for communication.

6. System according to claim 1, characterized in that the interfaces are galvanically insulated from associated instruments.

7. System according to claim 1, characterized in that one of the instruments connected to the bus is a remote controller for at least one instrument.

8. A system according to claim 7 and comprising a remote controller connected to the bus said remote controller having controls for more than one instrument and for self configuring to each said instrument to be controlled.

9. System according to claim 8, characterized in that said remote controller is so structured that it is suitable for application under sterile conditions.

10. System according to claim 7, characterized in that changes of settings of instruments which are made via said remote controller are graphically displayed.

11. System according to claim 1, characterized in that said bus master is selected from one of a group of instruments consisting of:
    a video signal processor instrument,
    a master computer,
    a remote controller unit,
    a network module, and
    combinations thereof.

12. System according to claim 11,
    characterised in that said network module is adapted for being connected and specifically docked to each unit connectable to the bus.

13. System according to claim 1, characterized in that the BUS master is a personal computer.

14. System according to claim 13, characterized in that said personal computer is programmed to operate in a programming mode and in an application or communication mode.

15. System according to claim 14, characterized in that in the programming mode operating parameters of instruments to be controlled may be preset and stored as preset values, and that in the application mode operating parameters can be changed only currently without any influence on a fundamental setting.

16. System according to claim 15, characterized in that for each instrument to be controlled several different presettings are stored to be called in by an operator as needed.

17. System according to claim 16,
    characterised in that merely specific parameters of the units connected to the bus can be changed in correspondence with the respectively called-in presetting.

18. System according to claim 15, characterized in that activation of the programming mode excludes execution of a treatment procedure.

19. System according to claim 13, characterized in that the personal computer comprises a graphic user interface.

20. System according to claim 19, characterized in that said graphic user interface displays operating elements of at least one instrument on a monitor.

21. System according to claim 20, characterized in that said graphic user interface simultaneously displays operating elements of several instruments.

22. System according to claim 20, characterized in that the operating elements are so configured that operation of the instrument under sterile conditions is possible.

23. System according to claim 13, characterized in that the bus exchanges data with said personal computer via hardware selected from the group consisting of a serial interface, a FIFO, and a dual ported RAM.

24. System according to claim 1, characterized in that a speech-input and processing module is provided to control functions via the self-configuring bus.

25. System according to claim 24,
    characterised in that the speech commands are graphically displayed on a monitor or confirmed acoustically.

26. System according to claim 25,
    characterised in that commands or control procedures which have been incorrectly input can be cancelled immediately.

27. System according to claim 1, characterized in that a video signal processing unit, a video camera and a control computer are coupled to the self-configuring bus.

28. System according to claim 27,
    characterised in that said video camera is an analog or digital video camera.

29. System according to claim 27, characterized in that said video signal processing unit digitizes an image taken by said video camera and stores it in said control computer, said control computer being adapted for storing also general patient data as well as parameters of instruments with cross reference to the stored image.

30. System according to claim 27, characterized in that said video signal processing unit comprises a microprocessor which controls video signal processing and also a graphics processor to overlay data onto the image.

31. System according to claim 1, characterized in that a change of settings on an instrument is graphically displayed.

32. System according to claim 1, characterized in that at least two instruments are interconnected via the self-configuring bus to form a closed-loop control circuit.

33. System according to claim 32 characterized in that the closed-loop control circuit established via the bus superimposes an internal instrument control.

34. System according to claim 33, characterized in that the closed-loop control circuit established via the bus has a substantially slower time response than said internal instrument control.

35. System according to claim 32, characterized in that the instruments interconnected via the bus to form a closed-loop control circuit are selected from the group consisting of:

an insufflator, a suction means, a light source, a video camera, a pressure gauge, a pump, an insufflator, and combinations thereof.

36. System according to claim 1, characterized in that a bus monitor ing function is provided for triggering an alarm upon failure of said bus.

37. System according to claim 1, characterized in that software to unambiguously identify a user of the system.

38. System according to claim 37, characterised in that the input of the respective user changes the fundamental setting of the system.

39. System according to claim 1, characterized in that software to individually configure an instrument connected to the self-configuring bus.

40. System according to claim 39, characterized in that software is included to store preset values associated with respective instruments that are connected to the bus via interfaces.

* * * * *